(12) United States Patent
Michiels et al.

(10) Patent No.: US 6,333,449 B1
(45) Date of Patent: Dec. 25, 2001

(54) GLUFOSINATE TOLERANT RICE

(75) Inventors: Frank Michiels, Bottelare (BE); Kirk Johnson, Davis, CA (US)

(73) Assignee: Plant Genetic Systems, N.V., Gent (BE)

( * ) Notice: Subject to any disclaimer, the term of this patent is extended or adjusted under 35 U.S.C. 154(b) by 0 days.

(21) Appl. No.: 09/185,244

(22) Filed: Nov. 3, 1998

(51) Int. Cl.⁷ .................. A01H 5/00; A01H 5/10; C12N 5/14; C12N 15/82
(52) U.S. Cl. .................. 800/300; 800/260; 800/278; 800/320.2; 435/418; 435/419; 47/58.1
(58) Field of Search .................. 800/295, 298, 800/278, 320.2, 300, 260; 536/24.1, 23.6; 435/419, 468, 418; 47/58.1

(56) References Cited

U.S. PATENT DOCUMENTS

| | | |
|---|---|---|
| 4,673,640 | 6/1987 | Backman . |
| 5,273,894 | 12/1993 | Strauch et al. . |
| 5,276,268 | 1/1994 | Strauch et al. . |
| 5,527,695 | 6/1996 | Hodges et al. . |
| 5,561,236 | 10/1996 | Leemans et al. . |
| 5,637,489 | 6/1997 | Strauch et al. . |
| 5,641,664 | 6/1997 | D'Halluin . |
| 5,646,024 | 7/1997 | Leemans et al. . |
| 5,679,558 | * 10/1997 | Gobel et al. . |
| 5,739,082 | 4/1998 | Donn . |

FOREIGN PATENT DOCUMENTS 0 275 957   3/1993   (EP) .

OTHER PUBLICATIONS

"Engineering herbicide resistance in plants by expression of a detoxifying enzyme," Block et al., The EMBO Journal vol. 6, No. 9, pp 2513–2518, 1987.

"Rice weed control: current technology and emerging issues in temperate rice," Hill et al., Australian Journal of Experimental Agriculture, 1994, 34, 1021–9.

"Characterization of the herbicide–resistance gene bar *Streptomyces hugroscopicus*," Thompson et al., The EMBO Journal, vol. 6 No. 9, pp. 2519–2523, 1987.

"Nucleotide sequence of the phosphinothricin N–acetyl-transferase gene from *Streptomyces viridochromogenes* Tü494 and its expression in *Nicotiana tabacum*," Wohlleben et al., Gene, 70 (1988) 25–37 Elsevier.

"Production of transgenic rice (*oryza sativa L.*) plants from agronomically important indica and japonica varieties via electric discharge particle acceleration of exogenous DNA into immature zygotic embryos," Christou et al., BioTechnology vol. 9, Oct. 1991, pp 957–962.

\* cited by examiner

*Primary Examiner*—Amy J. Nelson
*Assistant Examiner*—David H. Kruse
(74) *Attorney, Agent, or Firm*—Frommer Lawrence & Haug LLP

(57) ABSTRACT

The invention relates to an elite event glufosinate tolerant rice plant transformed with a bar gene, such as a 35S-bar gene, where the gene is inserted into the location defined by SEQ ID [No] NO: 9 within the rice genome, and methods of making and using the glufosinate tolerant rice plant.

19 Claims, 2 Drawing Sheets

SEQUENCE LISTING

```
<160> NUMBER OF SEQ ID NOS: 9

<210> SEQ ID NO 1
<211> LENGTH: 113
<212> TYPE: DNA
<213> ORGANISM: Artificial Sequence
<220> FEATURE:
<223> OTHER INFORMATION: Description of Artificial Sequence: sequence
      comprising 5' flanking region of transgene in
      GAT-OS2
<220> FEATURE:
<221> NAME/KEY: primer_bind
<222> LOCATION: (56)..(76)
<223> OTHER INFORMATION: primer YTP059
<220> FEATURE:
<221> NAME/KEY: misc_feature
<222> LOCATION: (1)..(92)
<223> OTHER INFORMATION: plant DNA
<220> FEATURE:
<221> NAME/KEY: misc_feature
<222> LOCATION: (93)..(113)
<223> OTHER INFORMATION: transgene

<400> SEQUENCE: 1
agtttgcata gttgggggtg aagaatgccc gattttgtgg tttagggggg gtaattcgga        60
caaccgcgat agttcggggg taattagtac ttttgcatgc ctgcaggtcg act             113

<210> SEQ ID NO 2
<211> LENGTH: 1279
<212> TYPE: DNA
<213> ORGANISM: Artificial Sequence
<220> FEATURE:
<223> OTHER INFORMATION: Description of Artificial Sequence: sequence
      comprising 3' flanking region of transgene in
      GAT-OS2
<220> FEATURE:
<221> NAME/KEY: primer_bind
<222> LOCATION: (1)..(20)
<223> OTHER INFORMATION: primer MDB424
<220> FEATURE:
<221> NAME/KEY: primer_bind
<222> LOCATION: (247)..(268)
<223> OTHER INFORMATION: primer MDB442
<220> FEATURE:
<221> NAME/KEY: primer_bind
<222> LOCATION: (354)..(374)
<223> OTHER INFORMATION: primer MDB410
<220> FEATURE:
<221> NAME/KEY: primer_bind
<222> LOCATION: (406)..(426)
<223> OTHER INFORMATION: primer OSA03
<220> FEATURE:
<221> NAME/KEY: primer_bind
<222> LOCATION: Complement((1254)..(1274))
<223> OTHER INFORMATION: primer YTP66
<220> FEATURE:
<221> NAME/KEY: primer_bind
<222> LOCATION: Complement((697)..(717))
<223> OTHER INFORMATION: primer OSA04
```

```
<220> FEATURE:
<221> NAME/KEY: misc_feature
<222> LOCATION: (2)..(604)
<223> OTHER INFORMATION: transgene
<220> FEATURE:
<221> NAME/KEY: misc_feature
<222> LOCATION: (605)..(1279)
<223> OTHER INFORMATION: plant DNA

<400> SEQUENCE: 2
aaggatagtg ggattgtgcg tcatcccTta cgtcagtgga gatatcacat caatccactt    60
gctttgaaga cgtggttgga acgtcttctt tttccacgat gctcctcgtg ggtgggggtc   120
catctttggg accactgtcg gcagaggcat cttcaacgat ggccttTcct ttatcgcaat   180
gatggcattt gtaggagcca ccttcctttt ccactatctt cacaataaag tgacagatag   240
ctgggcaatg gaatccgagg aggtttccgg atattaccct ttgttgaaaa gtctcaattg   300
cccttTggtc ttctgagact gtatctttga tattTtTgga gtagacaagc gtgtcgtgct   360
ccaccatgtt gacgaagatt ttcttcttgt cattgagtcg taagagactc tgtatgaact   420
gttcgccagt ctttacggcg agttctgtta ggtcctctat ttgaatcttt gactccatgg   480
gaattcactg gccgtcgttt tacaacgtcg tgactgggaa accctggcg ttacccaact    540 taatcgcctt gcagcacatc cccctttcgc cagctggcgt aatagcgaag aggcccgcac   600
cgattattta actttTagt ccacctggtt tttattgata gacgatgcac ccgttagcag   660
taagacatcg ctaaatcttT ggaagtaggt gagtgtgcgt gttacataca tatgcgacat   720
atttcttaag atctttgttT taagaaaaac caacttctca caacaaacga attagttttg   780
agattgttgt gttggaggga ccgtagtcgc cgttgcttcc ggtcagcacc gtggcctagc   840
aggagagcgt ccgagaaggg cctaattggg acgcacgatg tggtcacggg ccttttgggg   900
taacgcgcac acggcccatc cggtttccct gctgcatcgc gcggcacgcg acgcaacacc   960
ggtccactta ttgatcTtat agccaagcTt gattcacttg gcacgaagtc aagatggccg  1020
agttggtcta aggcgccagt ttcaggtact ggtccgaaag ggcatgggtt cgaatcccat  1080
tcttgacaat atttTTTTTg accTtgggtt gggttcgaat cccattcttg acattgttTT  1140
ttTTccttTg tttaaattta accatttaac cgcggccaaa aatttTaaTT ttttTtgctT  1200
tgttttaacc acaccacggc caaaaattTt aaaattttTT tgctttgttT taaccacggt  1260
caaaattaac acggacaaa                                                1279

<210> SEQ ID NO 3
<211> LENGTH: 168
<212> TYPE: DNA
<213> ORGANISM: Artificial Sequence
<220> FEATURE:
<223> OTHER INFORMATION: Description of Artificial Sequence: sequence
      comprising insertion site as derived from GAT-OS2
<220> FEATURE:
<221> NAME/KEY: primer_bind
<222> LOCATION: (1)..(21)
<223> OTHER INFORMATION: primer YTP057
<220> FEATURE:
<221> NAME/KEY: primer_bind
<222> LOCATION: (147)..(168)
<223> OTHER INFORMATION: primer OSA04
<220> FEATURE:
<221> NAME/KEY: misc_feature
<222> LOCATION: (38)..(55)
<223> OTHER INFORMATION: target site deletion

<400> SEQUENCE: 3
tcggacaacc gcgatagttc gggggtaatt agtacttttT ccttatattt atgactatTt    60
```

-continued

```
atacttttag tccacctggt ttttattgat agacgatgca cccgttagca gtaagacatc      120
gctaaatctt tggaagtagg tgagtgtgcg tgttacatac atatgcga                  168
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer
      OSA03 (target: P35S)

<400> SEQUENCE: 4

```
gactctgtat gaactgttcg c                                               21
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: OSA04:
      GAT-OS2-specific PRIMER (target: plant DNA)

<400> SEQUENCE: 5

```
tcgcatatgt atgtaacacg c                                               21
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: OSA01: rice
      endogenous primer 1

<400> SEQUENCE: 6

```
gatcagtgca ggcaatactg g                                               21
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: OSA02: rice
      endogenous primer 2

<400> SEQUENCE: 7

```
ttcctaacat gtgggtgtcg                                                 20
```

<210> SEQ ID NO 8
<211> LENGTH: 4161
<212> TYPE: DNA
<213> ORGANISM: Artificial Sequence
<220> FEATURE:
<223> OTHER INFORMATION: Description of Artificial Sequence: plasmid
      pB5/35Sbar

<400> SEQUENCE: 8

```
cggctccgtc gatactatgt tatacgccaa ctttgaaaac aactttgaaa aagctgtttt      60 ctggtatttta aggttttaga atgcaaggaa cagtgaattg gagttcgtct tgttataatt    120
agcttcttgg ggtatctttα aatactgtag aaaagaggaa ggaaataata aatggctaaa    180
atgagaatat caccggaatt gaaaaaactg atcgaaaaat accgctgcgt aaaagatacg    240
gaaggaatgt ctcctgctaa ggtatataag ctggtgggag aaaatgaaaa cctatattta    300
aaaatgacgg acagccggta taagggacc acctatgatg tggaacggga aaggacatg     360
```

-continued

```
atgctatggc tggaaggaaa gctgcctgtt ccaaaggtcc tgcactttga acggcatgat    420
ggctggagca atctgctcat gtgtgaggcc gatggcgtcc tttgctcgga agagtatgaa    480
gatgaacaaa gccctgaaaa gattatcgag ctgtatgcgg agtgcatcag gctctttcac    540
tccatcgaca tatcgggttg tccctatacg aatagcttag acagccgctt agccgaattg    600
gattacttac tgaataacga tctggccgat gtggattgcg aaaactggga agaagacact    660
ccatttaaag atccgcgcga gctgtatgat tttttaaaga cggaaaagcc cgaagaggaa    720
cttgtctttt cccacggcga cctgggagac agcaacatct ttgtgaaaga tggcaaagta    780
agtggcttta ttgatcttgg gagaagcggc agggcggaca gtggtatgca cattgccttc    840
tgcgtccggt cgatcaggga ggatatcggg gaagaacagt atgtcgagct attttttgac    900
ttactgggga tcaagcctga ttgggagaaa ataaaatatt atattttact ggatgaattg    960
ttttagtacc tagatgtggc gcaacgatgc cggcgacaag caggagcgca ccgacttctt   1020
ccgcaaaaag gatctaggtg aagatccttt ttgataatct catgaccaaa atcccttaac   1080
gtgagttttc gttccactga gcgtcagacc ccgtagaaaa gatcaaagga tcttcttgag   1140
atcctttttt tctgcgcgta atctgctgct tgcaaacaaa aaaaccaccg ctaccagcgg   1200
tggtttgttt gccggatcaa gagctaccaa ctctttttcc gaaggtaact ggcttcagca   1260
gagcgcagat accaaatact gttcttctag tgtagccgta gttaggccac cacttcaaga   1320
actctgtagc accgcctaca tacctcgctc tgctaatcct gttaccagtg gctgctgcca   1380
gtggcgataa gtcgtgtctt accgggttgg actcaagacg atagttaccg gataaggcgc   1440
agcggtcggg ctgaacgggg ggttcgtgca cacagcccag cttggagcga acgacctaca   1500
ccgaactgag atacctacag cgtgagctat gagaaagcgc cacgcttccc gaagggagaa   1560
aggcggacag gtatccggta agcggcaggg tcggaacagg agagcgcacg agggagcttc   1620 caggggggaaa cgcctggtat ctttatagtc ctgtcgggtt tcgccacctc tgacttgagc   1680
gtcgattttt gtgatgctcg tcaggggggc ggagcctatg gaaaaacgcc agcaacgcgg   1740
cctttttacg gttcctggcc ttttgctggc cttttgctca catgttcttt cctgcgttat   1800
cccctgattc tgtggataac cgtattaccg cctttgagtg agctgatacc gctcgccgca   1860
gccgaacgac cgagcgcagc gagtcagtga gcgaggaagc ggaagagcgc ccaatacgca   1920
aaccgcctct ccccgcgcgt tggccgattc attaatgcag ctggcacgac aggtttcccg   1980
actggaaagc gggcagtgag cgcaacgcaa ttaatgtgag ttagctcact cattaggcac   2040
cccaggcttt acactttatg cttccggctc gtatgttgtg tggaattgtg agcggataac   2100
aatttcacac aggaaacagc tatgaccatg attacgccaa gcttgcatgc ctgcaggtcg   2160
actctagagg atccccgggt accgagctcg aattcgagct cgccctggat tttggtttta   2220
ggaattagaa attttattga tagaagtatt ttacaaatac aaatacatac taagggtttc   2280
ttatatgctc aacacatgag cgaaacccta taagaaccct aattcccttat ctgggaact   2340 actcacacat tattatagag agagatagat ttgtagagag agactggtga tttcagcggg   2400
catgcctgca ggtcgactca gatctcggtg acgggcagga ccggacgggg cggtaccggc   2460
aggctgaagt ccagctgcca gaaacccacg tcatgccagt tcccgtgctt gaagccggcc   2520
gcccgcagca tgccgcgggg ggcatatccg agcgcctcgt gcatgcgcac gctcgggtcg   2580
ttgggcagcc cgatgacagc gaccacgctc ttgaagccct gtgcctccag ggacttcagc   2640
aggtgggtgt agagcgtgga gcccagtccc gtccgctggt ggcgggggga gacgtacacg   2700
```

-continued

```
gtcgactcgg ccgtccagtc gtaggcgttg cgtgccttcc aggggcccgc gtaggcgatg      2760
ccggcgacct cgccgtccac ctcggcgacg agccagggat agcgctcccg cagacggacg      2820
aggtcgtccg tccactcctg cggttcctgc ggctcggtac ggaagttgac cgtgcttgtc      2880
tcgatgtagt ggttgacgat ggtgcagacc gccggcatgt ccgcctcggt ggcacggcgg      2940
atgtcggccg ggcgtcgttc tgggctcatt gttggatccg gtaccctgtc ctctccaaat      3000
gaaatgaact tccttatata gaggaagggt cttgcgaagg atagtgggat tgtgcgtcat      3060
cccttacgtc agtggagata tcacatcaat ccacttgctt tgaagacgtg gttggaacgt      3120 cttcttttc cacgatgctc ctcgtgggtg ggggtccatc tttgggacca ctgtcggcag      3180
aggcatcttc aacgatggcc tttcctttat cgcaatgatg gcatttgtag gagccacctt      3240 cctttccac tatcttcaca ataaagtgac agatagctgg gcaatggaat ccgaggaggt      3300
ttccggatat tacccttttgt tgaaaagtct caattgccct ttggtcttct gagactgtat      3360
ctttgatatt tttggagtag acaagcgtgt cgtgctccac catgttgacg aagattttct      3420
tcttgtcatt gagtcgtaag agactctgta tgaactgttc gccagtcttt acggcgagtt      3480
ctgttaggtc ctctatttga atctttgact ccatgggaat tcactggccg tcgttttaca      3540
acgtcgtgac tgggaaaacc ctggcgttac ccaacttaat cgccttgcag cacatccccc      3600
tttcgccagc tggcgtaata gcgaagaggc ccgcaccgat cgcccttccc aacagttgcg      3660
cagcctgaat ggcgaatggc gcctgatgcg gtattttctc cttacgcatc tgtgcggtat      3720
ttcacaccgc atatgtggca ggatatatac cgttgtaatt tgagcataag tcgctgtgta      3780
tgtttgtttg catatggtgc actctcagta caatctgctc tgatgccgca tagttaagcc      3840
agccccgaca cccgccaaca cccgctgacg cgccctgacg gcttgtctg ctcccggcat       3900 ccgcttacag acaagctgtg accgtctccg ggagctgcat gtgtcagagg ttttcaccgt      3960
catcaccgaa acgcgcgaga cgaaagggcc tcgtgatacg cctatttttta taggttaatg     4020 tcatgataat aatggtttct tagacgtcag gtggcacttt tcggggaaat gtgcgcggaa      4080
cccctatttg tttatttttc taaatacatt caaatatgta ccgctcatg agacaataac       4140 cctgataaat gcttcaataa t                                                4161
```

<210> SEQ ID NO 9
<211> LENGTH: 785
<212> TYPE: DNA
<213> ORGANISM: Artificial Sequence
<220> FEATURE:
<223> OTHER INFORMATION: Description of Artificial Sequence: insertion region

<400> SEQUENCE: 9

```
agtttgcata gttgggggtg aagaatgccc gattttgtgg tttagggggg gtaattcgga       60
caaccgcgat agttcggggg taattagtac ttttccctta tatttatgac tatttatact     120
tttagtccac ctggtttta ttgatagacg atgcacccgt tagcagtaag acatcgctaa      180
atctttggaa gtaggtgagt gtgcgtgtta catacatatg cgacatattt cttaagatct     240
ttgttttaag aaaaaccaac ttctcacaac aaacgaatta gttttgagat tgttgtgttg     300
gagggaccgt agtcgccgtt gcttccgtc agcaccgtgg cctagcagga gagcgtccga     360
gaagggccta attgggacgc acgatgtggt cacgggcctt tggggtaac gcgcacacgg      420 cccatccggt ttccctgctg catcgcgcgg cacgcgacgc aacaccggtc cacttattga     480
tcttatagcc aagcttgatt cacttggcac gaagtcaaga tggccgagtt ggtctaaggc     540
```

-continued

```
gccagtttca ggtactggtc cgaaagggca tgggttcgaa tcccattctt gacaatattt     600
tttttgacct tgggttgggt tcgaatccca ttcttgacat tgttttttt cctttgttta     660 aatttaacca tttaaccgcg gccaaaaatt ttaattttt ttgctttgtt ttaaccacac     720
cacggccaaa aattttaaaa ttttttgct ttgttttaac cacggtcaaa attaacacgg     780
acaaa                                                               785
```

GLUFOSINATE TOLERANT RICE

FIELD OF THE INVENTION

This invention pertains to rice plants, plant material and seeds characterized by harboring a specific transformation event particularly by the presence of the bar gene under control of a CaMV 35S promoter, at a specific location in the rice genome. The rice plants of the invention combine glufosinate tolerance with optimal overall agronomic performance, genetic stability and adaptability to different genetic backgrounds.

All documents cited herein are hereby incorporated herein by reference.

BACKGROUND OF THE INVENTION

The phenotypic expression of a transgene in a plant is determined both by the structure of the gene itself and by its location in the plant genome. At the same time the presence of the transgene at different locations in the genome will influence the overall phenotype of the plant. The agronomically or industrially successful introduction of a commercially interesting trait in a plant by genetic manipulation can be a lengthy procedure dependent on different factors. The actual transformation and regeneration of genetically transformed plants are only the first in a series of selection steps which include extensive genetic characterization, breeding, and evaluation in field trials.

Rice production is commonly threatened by various weeds. Some of these can be highly competitive and in cases of severe infestation can result in yield loss of such magnitude that it makes the crop economically unattractive. For direct-seeded, mechanized rice cultivation typical of temperate production, both cultural practices (e.g. crop rotation, irrigation management) and herbicides are necessary to control weeds (Hill et al. 1994).

The bar gene (Thompson et al, 1987, EMBO J. 6:2519–2523; Deblock et al. 1987, EMBO J. 6:2513–2518) is a gene encoding the enzyme phosphinothricin acetyl transferase (PAT), which, when expresssed in a plant, confers resistance to the herbicidal compounds phosphinothricin (also called glufosinate) or bialaphos (see also for example U.S. Pat. Nos. 5,646,024 and 5,561,236) and salts and optical isomers thereof. Other genes encoding PAT have been described (see for example: Wohileben et al., 1988, Gene 70:25–37; EP 275,957; U.S. Pat. No. 5,276,268; U.S. Pat. No. 5,637,489; U.S. Pat. No. 5,273,894). The transformation of monocotyledonous plants by electroporation of intact tissue capable of forming compact embryogenic callus or compact embryogenic callus obtained from such tissue is described in U.S. Pat. No. 5,641,664. Herein, transformation of compact embryogenic callus of rice by electroporation of a bar gene and the regeneration of transgenic rice plants is disclosed.

Transgenic rice plants containing the gus gene with either the bar gene, or the hyg gene conferring resistance to hygromycin, obtained by the transformation of cells of immature rice embryos by bombardment with DNA-coated gold particles have been described (Christou et al, 1991: Biotechnology 9:957).

Transformation of rice with the bar gene by electroporation of aggregated suspension cells is described in U.S. Pat. No. 5,679,558.

However, the foregoing documents fail to teach or suggest the present invention.

SUMMARY OF THE INVENTION

The present invention relates to a transgenic, glufosinate tolerant rice plant, cell, tissue or seed, which is characterized by one or both of the following characteristics:

a) the genomic DNA of the plant, cell, tissue or seed is capable of yielding one or more, such as at least two, advantageously at least three, preferably at least four, for instance at least five, more preferably six of the restriction fragments or pairs of restriction fragments selected from the group of:

i) one EcoRI fragment with a length between about 1159 and about 1700 bp, preferably of about 1327 bp;

ii) one pair of BamHI fragments wherein one has a length between about 805 and about 1093 bp, preferably of about 805 bp and the other has a length between about 1700 and about 2140 bp, preferably of about 2,0 kbp;

iii) one pair of EcoRV fragments wherein one has a length between about 2838 and about 4507 bp, preferably of about 3,8 kbp and the other has a length of more than about 5077 bp, preferably of about 12 kbp;

iv) one HindIII fragment with a length between about 5077 and about 11497 bp, preferably of about 5,3 kbp;

v) one pair of NcoI fragments both with lengths between about 2838 and about 4507 bp, preferably one of about 3,1 kbp and one of about 4,1 kbp;

vi) one NsiI fragment with a length between about 4749 and about 11497 bp, preferably of about 5,1 kbp; wherein each of the restriction fragments is capable of hybridizing under standard stringency conditions, with the about 1327 bp fragment obtainable by EcoRI digestion of the plasmid having the nucleotide sequence of SEQ ID No 8; and/or, b) the genomic DNA of the plant, cell, tissue or seed can be used to amplify a DNA fragment of between 290 and 350 bp, preferably of about 313 bp, using a polymerase chain reaction with two primers having the nucleotide sequence of SEQ ID No 4 and SEQ ID No 5 respectively (or includes a DNA fragment of about 290 to about 350 bp, preferably of about 313 bp amplified using a polymerase chain reaction with two primers having the nucleotide sequence of SEQ ID No 4 and SEQ ID No 5 respectively).

The present invention relates to a transgenic, glufosinate tolerant rice plant, cell, tissue or seed, which is characterized in that the genomic DNA of the plant, cell, tissue or seed is capable of yielding at least one, advantageously at least two or more, for instance at least three, preferably at least four, for instance at least five, more preferably six of the restriction fragments or pairs of restriction fragments selected from the group described above comprising the restriction fragments or pairs of restriction fragments described under i), ii), iii), iv), v) and vi) above, whereby the selection can include any combination of i), ii), iii), iv), v) and vi) described above.

The present invention relates to a transgenic, glufosinate tolerant rice plant, cell, tissue or seed which is preferably characterized by both of the characteristics described under a) and b) above.

The invention also relates to the seed deposited at the ATCC under number ATCC 203352, a plant which is grown from this seed, and cells or tissues from a plant grown from this seed. The invention further relates to plants obtainable by propagation of, and/or breeding with a rice plant grown from the seed deposited at the ATCC under number ATCC 203352.

The invention further relates to plants, seeds, cells or tissues (e.g., rice plants, seeds, cells or tissues) comprising herein discussed flanking regions with the 35S-bar gene (as herein discussed) therebetween, or plants, seeds, cells, or tissues (e.g., rice plants, seeds, cells or tissues) comprising a nucleotide sequence which is at least 65%, e.g., at least 75%, such as at least 80%, for instance at least 85%, such as at least 90%, for example at least 95% or even 97% or 100% similar to a sequence disclosed herein, such as the sequence for the flanking region-35S-bar gene-flanking region construct, or the insertion region.

The invention further relates to a process for cultivating rice plants of the invention as described above, more particularly a process which comprises applying a herbicide with glufosinate as an active ingredient to the cultivated rice plants.

It is believed that the rice plants of the invention, when cultivated according to the process described above, which comprises applying a herbicide with glufosinate as an active ingredient, display improved growth as compared to untransformed rice of the same cultivar (U.S. Pat. No. 5,739,082). Thus, the invention can comprehend a method for improving the yield or growth of rice plants.

The invention also provides a process for breeding rice which comprises a crossing with the rice plants of the invention.

The invention further provides a process for producing a transgenic cell of a rice plant or a plant obtained therefrom, which comprises inserting a recombinant DNA molecule into a part of the chromosomal DNA of a rice cell characterized by the sequence of SEQ ID No 9 and, optionally, regenerating a rice plant from the transformed rice cell.

BRIEF DESCRIPTION OF THE DRAWINGS

The following detailed description, given by way of example, but not intended to limit the invention to specific embodiments described, may be understood in conjunction with the accompanying Figures, incorporated herein by reference, in which.

DETAILED DESCRIPTION

Figure 1:
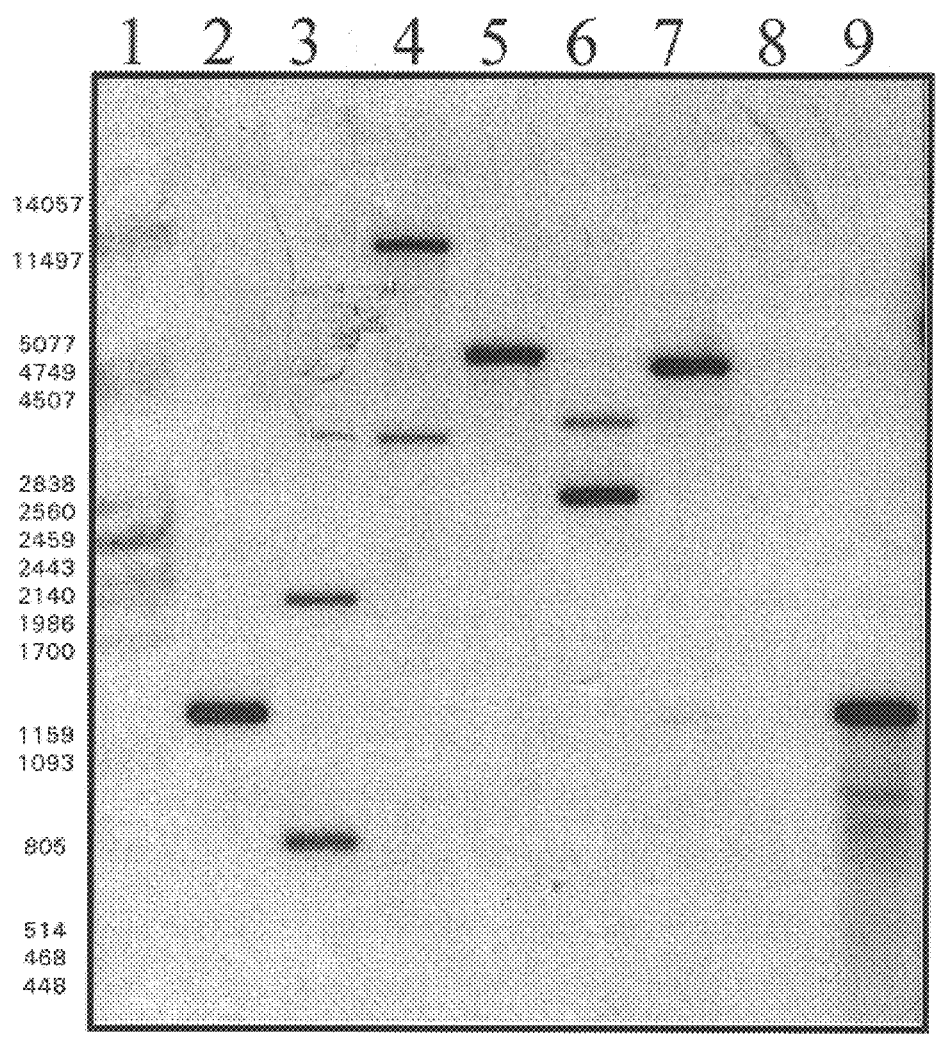
FIG. 1. Restriction map obtained after digestion of GAT-OS2 genomic DNA Loading sequence of the gel analyzed by Southern blot: lane 1, Lambda DNA digested with PstI, lane 2, GAT-OS2 DNA digested with EcoRI, lane 3, GAT-OS2 DNA digested with BamHI, lane 4, GAT-OS2 DNA digested with EcoRV, lane 5, GAT-OS2 DNA digested with HindIII, lane 6, GAT-OS2 DNA digested with NcoI, lane 7, GAT-OS2 DNA digested with NsiI, lane 8, non-transgenic rice DNA, lane 9, Control plasmid DNA digested with EcoRI.

The term "gene" as used herein refers to any DNA sequence comprising several operably linked DNA fragments such as a promoter and a 5' untranslated region (the 5'UTR), which together form the promoter region, a coding region (which may or may not code for a protein), and an untranslated 3' region (3'UTR) comprising a polyadenylation site. Typically in plant cells, the 5'UTR, the coding region and the 3'UTR are transcribed into a RNA which, in the case of a protein encoding gene, is translated into the protein. A gene may include additional DNA fragments such as, for example, introns. As used herein, a genetic locus is the position of a given gene in the genome of a plant.

The term "chimeric" when referring to a gene or DNA sequence is used to refer to the fact that the gene or DNA sequence comprises at least two functionally relevant DNA fragments (such as promoter, 5'UTR, coding region, 3'UTR, intron) that are not naturally associated with each other and originate, for example, from different sources. "Foreign" referring to a gene or a DNA sequence with respect to a plant species is used to indicate that the gene or DNA sequence is not naturally found in that plant species. As used herein the term "transgene" refers to a recombinant DNA molecule as incorporated in the genome of a plant. The term "recombinant DNA molecule" is used to exemplify and thus can include an isolated nucleic acid molecule which can be DNA and which can be obtained through recombinant or other procedures. This recombinant DNA molecule usually comprises at least one copy of at least one "gene of interest" (e.g. a chimeric gene) which is capable of conferring one or more specific characteristics to the transformed plant. A "transgenic plant" refers to a plant comprising a transgene in the genome of all of its cells.

The incorporation of a recombinant DNA molecule in the plant genome typically results from transformation of a cell or tissue (or from another genetic manipulation). The particular site of incorporation is either due to chance or is at a predetermined location (if a process of targeted integration is used).

The transgene can be characterized by the location and the configuration at the site of incorporation of the recombinant DNA molecule in the plant genome. The site in the plant genome where a transgene has been inserted is also referred to as the "insertion site" or "target site". Insertion of the transgene into the plant genome can be associated with a deletion of plant DNA, referred to as "target site deletion". A "flanking region" or "flanking sequence" as used herein refers to a sequence of at least 20 bp, preferably at least 50 bp, and up to 5000 bp of the plant genome which is located either immediately upstream of and contiguous with or immediately downstream of and contiguous with the transgene. Transformation procedures leading to random integration of the transgene will result in transformants with different flanking regions, which are characteristic and unique for each transformant. When the transgene is introduced into a plant through traditional crossing, its insertion site in the plant genome, or its flanking regions will generally not be changed. An "insertion region" as used herein refers to the region corresponding to the region encompassed by the insertion site (and possible target site deletion), the upstream and the downstream flanking regions of a transgene in the (untransformed) plant genome.

Expression of the transgene is used to indicate that the gene(s) of interest comprised in the transgene is expressed so as to confer on the plant one or more phenotypic traits (e.g. herbicide tolerance) that were intended to be conferred by the introduction of the recombinant DNA molecule—the transforming DNA—used during transformation (on the basis of the structure and function of part or all of the gene(s) of interest).

An event is defined as a (artificial) genetic locus that, as a result of genetic manipulation, carries a transgene comprising at least one copy of a gene of interest. The typical allelic states of an event are the presence or absence of the transgene. An event is characterized phenotypically by the expression of the transgene. At the genetic level, an event is part of the genetic makeup of a plant. At the molecular level, an event is characterized by the restriction map (e.g. as determined by Southern blotting) and/or by the upstream and/or downstream flanking sequences of the transgene, and/or the molecular configuration of the transgene. Usually transformation of a plant with a transforming DNA comprising at least one gene of interest leads to a multitude of events, each of which is unique.

An elite event, as used herein, is an event which is selected from a group of events obtained by transformation with the same transforming DNA, based on the expression and stability of the transgene and its compatibility with optimal agronomic characteristics of the plant comprising it. Thus the criteria for elite event selection are one or more, preferably two or more, advantageously all of the following:

a) That the presence of the transgene does not compromise other desired characteristics of the plant, such as those relating to agronomic performance or commercial value;

b) That the event is characterized by a well defined molecular configuration which is stably inherited and for which appropriate diagnostic tools for identity control can be developed;

c) That the gene(s) of interest in the transgene shows a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use;

It is preferred that the transgene is associated with a position in the plant genome that allows introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a transgene, which answers to the above-described criteria. A plant, plant material or progeny such as seeds can comprise the elite event in its genome.

The "diagnostic tools" developed to identify an elite event or the plant or plant material comprising an elite event, are based on the specific genomic characteristics of the elite event, such as, a specific restriction map of the genomic region comprising the transgene and/or the sequence of the flanking region(s) of the transgene. A "restriction map" as used herein refers to a set of Southern blot patterns obtained after cleaving plant genomic DNA with a particular restriction enzyme, or set of restriction enzymes and hybridization with a probe sharing sequence similarity with the transgene (under specific conditions). Due to the (endogenous) restriction sites present in a plant genome prior to incorporation of the transgene, insertion of a transgene will alter the specific restriction map of that genome. Thus, a particular transformant or progeny derived thereof can be identified by one or more specific restriction patterns. The conditions for determining the restriction map of an event are laid out in a restriction map identification protocol. Alternatively, once one or both of the flanking regions of the transgene have been sequenced, PCR-probes can be developed which specifically recognize this (these) sequence(s) in a PCR identification protocol. Plants or plant material comprising the elite event can be identified by testing according to the PCR identification protocol using these specific primers.

The term "similarity", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). The invention comprehends nucleic acid molecules and with sequences having at least 65%, e.g., at least 70%, such as at least 75%, or at least 80% or advantageously at least 85%, for instance at least 90%, such as at least 95% or even 97% or 100% similarity with sequences disclosed herein, as well as plants, cells, tissues, seeds, and progeny thereof (e.g., rice plants, cells, tissues, seeds and progeny thereof) comprising such . nucleic acid molecules. Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipmann algorithm (Wilbur and Lipman, 1983 PNAS USA 80:726) using a window size of 20 nucleotides, a word length of 4 nucleotides, and a gap penalty of 4, and computer-assisted analysis and interpretation of the sequence data including alignment can be conveniently performed using programs of the Intelligenetics™ Suite (Intelligenetics Inc. CA). Sequences which are "essentially similar" have a sequence similarity or identity of at least about 75%, advantageously at least about 80%, such as at least about 85%, preferably at least about 90%, especially about 95%, such as at least 97%, and especially about 100%. It is clear that when RNA sequences are said to be essentially similar or similar, or have a degree of sequence identity with DNA sequences, thymidine (T) in the DNA sequence is considered equal to uracil (U) in the RNA sequence.

The present invention relates to the development of an elite event in rice, GAT-OS2, and the plants, plant cells, or plant material derived from this event. Plants comprising elite event GAT-OS2 were obtained through transformation with a 1501 bp PvuI-HindIII fragment of plasmid pB5/35Sbar (SEQ ID No 8) as described in example 1.

The recombinant DNA molecule used for generation of this elite event comprises a DNA sequence encoding the enzyme phosphinothricin acetyl transferase and the 35S promoter of Cauliflower Mosaic Virus, wherein the sequence encoding phosphinothricin acetyl transferase is under the control of the 35S promoter of Cauliflower Mosaic Virus (termed the "35S-bar gene" ). The 35S promoter has a "constitutive" expression pattern in rice (Battraw et al, 1990, Plant Mol Biol 15:527–538), which means that it is significantly expressed in most plant cell types, during most of the plant life cycle. The expression of the 35S-bar gene in rice plants confers resistance to herbicidal compounds phosphinothricin or bialaphos or glufosinate or more generally, glutamine synthetase inhibitors, or salts or optical isomers thereof.

Plants or plant material comprising GAT-OS2 can be identified according to the restriction map identification protocol described in Example 3b)(1) herein. Briefly, rice genomic DNA is digested with a selection (preferably at least one such as at least two, advantageously at least three, or at least four, or at least five such as three to six) of the following restriction enzymes: EcoRI, BamHI, EcoRV, HindIII, NcoI, NsiI, is then transferred to nylon membranes and hybridized with the about1327 bp EcoRI fragment of plasmid pB5/35Sbar. It is then determined for each restriction enzyme used whether the following fragments can be identified:

EcoRI: one fragment of between about 1159 and about 1700 bp, preferably of about 1327 bp BamHI:one fragment of between about 1700 and about 2140 bp, preferably of about 2,0 kbp and one fragment of between about 805 and about 1093 bp, preferably of about 805 bp EcoRV: one fragment of more than about 5077 bp, preferably of about 12 kbp and one fragment of between about 2838 and about 4507 bp, preferably of about 3,8 kbp HindIII: one fragment of between about 5077 and about 11497 bp, preferably of about 5,3 kbp NcoI: two fragments of between about 2838 and about 4507 bp, preferably one of about 4,1 kbp and one of about 3,1 kbp NsiI: one fragment of between about 4749 and about 11497 bp, preferably of about 5,1 kbp.

The lengths of the DNA fragments are determined by comparison with a set of DNA fragments of known length, particularly the PstI fragments of phage lambda DNA.

If the plant material after digestion with at least one such as at least two, advantageously at least three, preferably at least four, especially with at least 5, more preferably with all of these restriction enzymes, yields DNA fragments with the same length as those described above, the rice plant is determined to harbor elite event GAT-OS2.

Plants or plant material comprising GAT-OS2 can also be identified according to the PCR identification protocol described in Example 3b)(2) herein. Briefly, rice genomic DNA is amplified by PCR using a primer which specifically recognizes a flanking sequence of GAT-OS2, particularly the primer with the sequence of SEQ ID No 5, and a primer which recognizes a sequence in the transgene, particularly the primer with the sequence of SEQ ID No 4. Endogenous rice primers are used as controls. If the plant material yields a fragment of between about 290 and about 350 bp, preferably of about 313 bp, the rice plant is determined to harbor elite event GAT-OS2.

Plants harboring GAT-OS2 are also characterized by their glufosinate tolerance, which in the context of the present invention includes that plants are tolerant to the herbicide Liberty™. Tolerance to Liberty™ is defined by the criterium that spraying of the plants in the three to four leaf stage (3V to 4V) with at least 200 grams active ingredient/hectare (g.a.i./ha), preferably 400 g.a.i./ha, and possibly up to 1600 g.a.i./ha, does not kill the plants. Plants harboring GAT-OS2 can further be characterized by the presence in their cells of phosphinothricin acetyl transferase as determined by a PAT assay (De Block et al, 1987, supra).

Plants harboring GAT-OS2 can, for example, be obtained from seeds deposited at the ATCC under number ATCC 203352. Such plants can be further propagated and/or used in a conventional breeding scheme to produce more transformed plants with the same characteristics or to introduce the elite event of the invention into other cultivars of the same plant species. Seeds obtained from these plants contain the elite event stably incorporated into their genome.

The rice plants of this invention can be cultivated in a conventional way. The presence of the transgene ensures that they are tolerant to glufosinate. Therefore, weeds in the fields where such rice plants are grown can be controlled by application of herbicides comprising glufosinate as an active ingredient (such as Liberty™).

Plants harboring GAT-OS2 are also characterized by having agronomical characteristics which are comparable to the following commercially available rice varieties in the US: Priscilla, Cypress, Bengal, Cocadrie, Jefferson, Madison, M202, M201, M103, Drew, Kaybonnet, Lagrue. The agronomical characteristics of relevance are: plant height, strength/stiffness of straw, resistance to lodging, leaf morphology (length, width, and angle for flag leaf), time to maturity, floret configuration, panicle fertility, complete closure of the hull on the seed, grain size and shape, and grain production and yield.

It has been observed that the presence of the transgene in this region of the rice plant genome, more particularly at this site in the rice plant genome, confers particularly interesting phenotypic and molecular characteristics to this event. More specifically, the presence of a transgene at this particular site in the genome results in stable phenotypic expression of the transgene without significantly compromising any aspect of desired agronomic performance of the plant. Thus, the insertion region, corresponding to SEQ ID No 9, more particularly the insertion site of GAT-OS2 therein, is shown to be particularly suited for the introduction of a gene(s) of interest, such as a herbicide resistance gene, more specifically a gene encoding phosphinothricin acetyl transferase under the control of a 35S promoter, particularly the PvuI-HindIII fragment of plasmid pB5/35Sbar.

A recombinant DNA molecule can be specifically inserted in this insertion region by targeted insertion methods. Such methods are well known to those skilled in the art and comprise, for example, homologous recombination using a recombinase such as, but not limited to either FLP recombinase from *Saccharomyces cervisiae* (U.S. Pat. No. 5,527, 695), the CRE recombinase from *Escherichia coli* phage P1 (published PCT application WO 9109957, the recombinase from pSRI of *Saccharomyces rouxii* (Araki et al. 1985, J Mol Biol 182:191–203), or the lambda phage recombination system such as described in U.S. Pat. No. 4,673,640.

DNA can be inserted into a plant genome, such as a rice genome by techniques including, electroporation methods, bombardment with DNA-coated gold particles or biolistic methods, or agrobacterium or polyethylene glycol mediated methods, and the like.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

The following examples describe the development and characteristics of rice plants harboring the elite event GAT-OS2.

Unless otherwise stated, all recombinant DNA techniques are carried out according to standard protocols as described in Sambrook et al. (1989) *Molecular Cloning: A Laboratory Manual*, Second Edition, Cold Spring Harbour Laboratory Press, NY and in Volumes 1 and 2 of Ausubel et al. (1994) *Current Protocols in Molecular Biology*, Current Protocols, USA. Standard materials and methods for plant molecular work are described in Plant Molecular Biology Labfax (1993) by R.D.D. Croy published by BIOS Scientific Publications Ltd (UK) and Blackwell Scientific Publications, UK.

In the description and examples, reference is made to the following sequences:

SEQ ID No 1: sequence comprising the 5' flanking region of GAT-OS2

SEQ ID No 2: sequence comprising the 3' flanking region of GAT-OS2

SEQ ID No 3: sequence comprising the insertion site of GAT-OS2

SEQ ID No 4: OSA03: primer of the PCR identification protocol

SEQ ID No 5: OSA04: GAT-OS2-specific primer of the PCR identification protocol

SEQ ID No 6: OSA01 rice endogenous primer

SEQ ID No 7: OSA02 rice endogenous primer

SEQ ID No 8: plasmid pB5/35Sbar
SEQ ID No 9: insertion region

EXAMPLES

Example 1

Transformation of Rice with a Gene Encoding Herbicide Resistance a) Construction of the Chimeric DNA Comprising the Bar Gene Under the Control of a 35S Promoter (pB5/35Sbar)

A plasmid pB5/35Sbar was constructed following standard procedures. The sequence of plasmid pB5/35Sbar is given in SEQ ID No 8. Digestion with PvuI-HindIII yielded a 1501 bp fragment which comprised the following genetic elements:

| Nucleotide coordinates | Genetic elements |
| --- | --- |
| 2140–2195 | Sequence derived from pUC19 (Yanish-Perron et al., Gene 33:103–119, 1985) |
| 2196–2204 | Synthetic polylinker sequence |
| 2205–2398 | Complement of 35S terminator (T35S) from Cauliflower Mosaic Virus (Franck A. et al., Cell 21:285–294, 1980; Pietrzak M. et al., Nucl. Acids Res. 14:5857–5868, 1986) |
| 2399–2417 | Synthetic polylinker sequence |
| 2418–2969 | Complement of bar gene from Streptomyces hygroscopicus (Thompson et al., EMBO J. 6:2519–2523, 1986) |
| 2970–2985 | Synthetic polylinker sequence |
| 2986–3517 | Complement of 35S promoter (P35S) from Cauliflower Mosaic Virus (Franck et al. above; Pietrzak et al., above) |
| 3518–3641 | Sequence derived from pUC19, (Yanisch-Perron et al., above) |

The 1501 bp PvuI-HindIII fragment was purified by extraction of this fragment after electrophoresis.

b) Transformation of Rice

The Bengal Variety is a medium-grain rice developed by the Rice Research Station of the Louisiana Agricultural Experiment Station. The variety was officially released in 1992. The pedigree includes MARS and M201 (Linscombe S. D. et al. 1993, Crop Science: 33:645–646).

Transformation of rice plants with the 1501 bp PvuI-HindIII fragment of pB5/35Sbar was performed using direct DNA transfer. Selection was done on phosphinothricin (PPT) at all stages except plantlet regeneration, which was done in the absence of PPT to accelerate growth. This resulted in a set of primary transformants (plants of generation $T_0$).

Example 2

Development of Events a) Development of Transgenic Homozygous Lines

The various $T_0$ hemizygous plantlets were transitioned from tissue culture, transferred to greenhouse soil, and allowed to flower and set seed. Plantlets were evaluated for fertility, fecundity and tolerance to glufosinate ammonium. 19 plants were selected for further analysis. $T_1$ seed produced by selfing was collected from these plants and grown in the field. $T_1$ plants were sprayed with Liberty™ herbicide at 800 grams active ingredient per hectare (g.a.i./ha; recommended dosage for farmers is 400 g.a.i./ha). The events that survived the herbicide application and segregated 3:1 for herbicide tolerance were selected for further evaluation. Tolerant plants were evaluated for damage (leaf tip burn). $T_2$ seeds were harvested from panicles of all tolerant plants of selected events. These were sown in rows and $T_2$ plants were sprayed with Liberty™ herbicide (1600 g.a.i./ha) to evaluate segregation of the herbicide tolerance. Those rows that had 100% survivors and thus corresponded to lines which were homozygous for the transgene were selected. These were again evaluated for herbicide damage and phenotypic traits. Further selection of events was made based on uniformity of phenotype within the panicle row (for the desired characteristics).

b) Characterization of Transgenic Events—Selection of GAT-OS2

Transgenic events were further characterized for southern blot patterns, general phenotype and agronomic performance, and yield. Where appropriate these characteristics were determined in field conditions.

Southern Blot Analysis

Presence of the transgene was checked by standard Southern blot analysis using enzymatic digestion of rice genomic DNA with EcoRV and hybridization to the 1327 bp EcoRi fragment of pB5/35Sbar. The relative band intensity provided an indication on whether plants were homozygous or hemizygous for the transgenic locus. Two events were found to have simple insertions. This was confirmed by the fact that the segregation pattern of the transgene could be explained by Mendelian inheritance of a simple locus.

General Plant Phenotype and Agronomic Performance $T_1$ and $T_2$ plants were evaluated for a number of phenotypic traits including plant height, strength/stiffness of straw, tendency to lodge, leaf morphology (too thin or incorrect angle for flag leaf), late maturity, floret configuration, panicle sterility or incomplete fertility, incomplete closure of the hull on the seed (which would lead to increased disease susceptibility), grain size and shape, and grain production and yield.

Lines were evaluated to be similar (or improved) in displayed agronomic characteristics compared to the untransformed Bengal cultivar and the following rice varieties: Priscilla, Cypress, Cocadrie, Jefferson, Madison, M202, M201, M103, Drew, Kaybonnet, Lagrue. In some cases, the plants within a panicle row segregated for somaclonal variation for one or more of the above-mentioned traits. Unless this resulted in the introduction of a commercially interesting phenotypic trait, these plants were discarded.

Field Trials for Yield Evaluation $T_2$ seeds were harvested in bulk from the selected homozygous populations and were compared to variety standards of Bengal. The seeds were planted as panicle rows in isolated blocks representing each event. Transgenic plots were sprayed with 1,600 g.a.i./ha of Liberty™ herbicide or not sprayed ("no-spray" plots). Plots with non-transgenic variety standards were not sprayed with Liberty™. Standard herbicide treatments to control local weeds were applied to all plots.

Transgenic events were tested for yield performance in different locations including Louisiana and Puerto Rico (winter nursery).

Statistical analysis of the agronomic parameters and ranking statistics of the plant morphology and other non-parametric data were completed to identify the best commercial candidate to compete with the parent variety, Bengal and the following rice varieties: Priscilla, Cypress, Cocadrie, Jefferson, Madison, M202, M201, M103, Drew, Kaybonnet, Lagrue. GAT-OS2 was the event showing the most utility for producing a range of breeding lines.

Example 3

Characterization of event GAT-OS2 a) In-depth Molecular and Genetic Analysis of the Locus

Once the GAT-OS2 event was identified as the event in which expression of the transgene as well as overall agronomic performance were optimal, the locus of the transgene was analyzed in detail on a molecular level. This included detailed Southern blot analysis and sequencing of the flanking regions of the transgene.

(1) Southern Blot Analysis Using Multiple Restriction Enzymes

Leaf tissue was harvested from transgenic and control plants. Total genomic DNA was isolated from leaf tissue according to Dellaporta et al. (1983, Plant Molecular Biology Reporter, 1, vol.3, p.19–21). The DNA concentration of each preparation was determined by measuring the optical density in a spectrophotometer at a wavelength of 260 nm.

10 µg of genomic DNA was digested with restriction enzyme in a final reaction volume of 40 µl, applying conditions proposed by the manufacturer. The time of digestion and/or amount of restriction enzyme were adjusted to ensure complete digestion of the genomic DNA samples without non-specific degradation. After digestion, 4 µl of loading dye was added to the digested DNA samples, and they were loaded on a 1% agarose gel.

The following control DNAs were also loaded on the gel:

a negative control with genomic DNA prepared from a non-transgenic rice plant. This negative control is used to confirm the absence of background hybridization.

a DNA positive control: With a heterozygous single copy integration of the transgene into the *Oryza sativa* genome, 10 µg of genomic DNA has the same number of molecule equivalents as±19 picogram of 1501 bp PvuI-HindIII fragment of pB5/35Sbar DNA (*Oryza sativa* diploid genome size: $0.8 \times 10^9$ bp). The amount representing one plasmid copy per genome is added to 1 µg of digested non-transgenic *Oryza sativa* DNA. This reconstitution sample is used to show that the hybridizations are performed under conditions allowing hybridization of the probe with target sequences. Phage Lambda DNA (strain Clind 1 ts 857 Sam 7, Life Technologies) digested with PstI was included as size standard.

After electrophoresis, the DNA samples (digested rice genomic DNA, controls and size standard DNA) were transferred to a Nylon membrane by capillary blotting during 12 to 16 hours. The DNA templates used for probe preparation were prepared by restriction digestion of plasmid pB5/35Sbar with EcoRI. This released a 1327 bp DNA fragment that encompasses a relevant part of the transforming DNA (1501 bp PvuI-HindIII fragment). After purification, the DNA fragment was labeled according to standard procedures, and used for hybridizing to the membrane.

Hybridization was performed under standard stringency conditions: The labeled probe was denaturated by heating for 5 to 10 minutes in a water bath at 95° C. to 100° C. and chilling on ice for 5 to 10 minutes and added to the hybridization solution (6×SSC (20×SSC is 3.0 M NaCl, 0.3 M Na citrate, pH 7.0), 5×Denhardt's (100×Denhardt's =2% Ficoll, 2% Polyvinyl pyrollidone, 2% Bovine Serum Albumin), 0.5% SDS and 20 µg/ml denatured carrier DNA (single-stranded fish sperm DNA, with an average length of 120–3000 nucleotides). The hybridization was performed overnight at 65° C. The blots were washed three times for 20 to 40 minutes at 65° C., with the wash solution (2×SSC, 0.1% SDS).

The autoradiographs were electronically scanned.

The restriction patterns obtained after digestion of GAT-OS2 genomic DNA with different restriction enzymes is presented in FIG. 1 and summarized in Table 1.

TABLE 1

Restriction map of GAT-OS2

| Lane number | DNA Loaded | Migration of hybridizing DNA fragments between size marker bands | | Estimated length of the hybridizing DNA fragments. |
|---|---|---|---|---|
| | | Larger than | Smaller than | |
| 1 | Lambda DNA with PstI | Not Applicable | Not Applicable | |
| 2 | GAT-OS2 - EcoRI | 1159 | 1700 | 1327 bp (*) |
| 3 | GAT-OS2 - BamHI | 1700 | 2140 | 2.0 kbp |
| | | 805 | 1093 | 805 bp (*) |
| 4 | GAT-OS2 - EcoRV | 5077 | — | 12 kbp |
| | | 2838 | 4507 | 3.8 kbp |
| 5 | GAT-OS2 - HindIII | 5077 | 11497 | 5.3 kbp |
| 6 | GAT-OS2 - NcoI | 2838 | 4507 | 4.1 kbp |
| | | 2838 | 4507 | 3.1 kbp |
| 7 | GAT-OS2 - NsiI | 4749 | 11497 | 5.1 kbp |
| 8 | Non-transgenic rice | — | — | — |
| 9 | Control plasmid DNA - EcoRI | 1159 | 1700 | 1327 bp |

(*) the lengths of these fragments are those predicted from the restriction map of the 1501 bp PvuI-HindIII fragment of pB5/35S.

(2) Identification of Flanking Sequences

The sequence of the regions flanking the inserted transgene in the GAT-OS2 event was determined using the thermal asymmetric interlaced (TAIL-) PCR method as described by Liu et al. (1995, The Plant Journal 8(3):457–463). This method utilizes three nested specific primers in successive reactions together with a shorter arbitrary degenerate (AD) primer so that the relative amplification efficiencies of specific and non-specific products can be thermally controlled. The specific primers were selected for annealing to the border of the transgene and based on their annealing conditions. A small amount (5 µl) of unpurified secondary and tertiary PCR products were analyzed on a 1% agarose gel. The tertiary PCR product was used for preparative amplification, purified and sequenced on an automated sequencer using the DyeDeoxy Terminator cycle kit.

1. TAIL-PCR of the HindIII site

The primers used were:

| | Sequence (5' → 3') | Position in pB5/35Sbar |
|---|---|---|
| Degenerate primer MDB556 | CNg.ASN.AgW.TWg.CAT.A | — |
| Primary TAIL MDB010 | gCA.CCA.TCg.TCA.ACC.ACT.ACA.TCg | 2905 → 2882 |
| Second. TAIL MDB559 | TTC.Tgg.Cag.CTg.gAC.TTC.AgC | 2483 → 2463 |
| Tertiary TAIL MDB411 | Agg.CAT.gCC.gCT.gAA.ATC.ACC | 2407 → 2386 | whereby: N = A, C, T or g; S = C or g; W = A or T

The fragment amplified using MDB556-MDB411 was ca. 400 bp of which 113 bp were sequenced (5'flank: SEQ ID No 1). The sequence between bp 1 and bp 92 comprised plant DNA, while the sequence between bp 93 and bp 113 corresponded to pB5/35Sbar DNA.

2. TAIL-PCR of the PvuI site
The primers used were:

| | Sequence (5' → 3') | Position in pB5/35Sbar |
|---|---|---|
| Degenerate primer MDB285 | NTC.gAS.TWT.SgW.gTT | — |
| Primary TAIL MDB424 | AAg.gAT.AgT.ggg.ATT.gTg.Cg | 3037 → 3056 |
| Secondary TAIL MDB442 | AAT.ggA.ATC.CgA.ggA.ggT.TTC.C | 3283 → 3304 |
| Tertiary TAIL MDB410 | TCg.TgC.TCC.ACC.Atg.TTg.ACg | 3390 → 3410 | whereby: N = A, C, T or g; S = C or g; W = A or T

The fragment amplified using MDB285-MDB410 was ca. 1200 bp (3'flank: SEQ ID No 2). The sequence between bp 1 and bp 604 corresponded to pB5/35Sbar DNA, while bp 605 to bp 1279 comprised plant DNA.

(3) Identification of the Target Site Deletion

Using primers corresponding to sequences within the flanking regions of the transgene on the wildtype *Oryza sativa* var. Bengal as a template, the insertion site of the transgene was identified.
The following primers were used:

| | Sequence (5' → 3') | Position in 5' flank (SEQ ID No 1) | Position in 3' flank (SEQ ID No 2) |
|---|---|---|---|
| YTP059 | TCg.gAC.AAC.CgC.gAT.AgT.Tcg | 56 → 76 | — |
| OSA04 | TCg.CAT.ATg.TAT.gTA.ACA.CgC | — | 717 → 697 |

This yielded a 168 bp fragment (SEQ ID No 3) in which bp 38 to 55 corresponds to a target site deletion. Thus, the complete rice insertion region (SEQ ID No 9) as sequenced comprises:

| 1–92: | 5' flanking region | bp 1–92 of SEQ ID No 1 |
|---|---|---|
| 93–110: | target site deletion | bp 38 to 55 of SEQ ID No 3 |
| 111–785: | 3' flanking region | bp 605 to 1279 of SEQ ID No 2 |

(4) Genetic Analysis of the Locus

The genetic stability of the insert was checked by molecular and phenotypic analysis in the progeny plants over several generations.

Southern blot analyses on glufosinate resistant plants of GAT-OS2 rice plants of the $T_0$, $T_1$ and $T_2$ generation were compared and were found to be identical. This proves that the molecular configuration of the transgene in GAT-OS2 containing plants was stable.

The GAT-OS2 event displayed Mendelian segregation for the transgene as a single genetic locus in at least three subsequent generations indicating that the insert is stable.

On the basis of the above results GAT-OS2 was identified as an elite event.

b) Development of Diagnostic Tools for Identity Control

The following protocols were developed to identify any rice plant material comprising the elite event GAT-OS2.

(1) GAT-OS2 Elite Event Restriction Map Identification Protocol

Rice plants containing the elite event GAT-OS2 can be identified by Southern blotting using essentially the same procedure as described in Example 3 a) (1). Thus rice genomic DNA is 1) digested with at least three, preferably at least 4, particularly with at least 5, more particularly with all of the following restriction enzymes: EcoRI, BamHI, EcoRV, HindIII, NcoI, NsiI, 2) transferred to nylon membranes and 3) hybridized with the 1327 bp EcoRI fragment of plasmid pB5/35Sbar. If, with respect to each of the restriction enzymes used, DNA fragments are identified with the same length as those listed in Table 1, the rice plant is determined to harbor elite event GAT-OS2.

(2) GAT-OS2 Elite Event Polymerase Chain Reaction Identification Protocol

A test run, with all appropriate controls, has to be performed before attempting to screen unknowns. The presented protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

Template DNA

Template DNA is prepared according to Edwards et al. (Nucleic Acid Research, 19, p1349, 1991). When using DNA prepared with other methods, a test run utilizing different amounts of template should be done. Usually 50 ng of genomic template DNA yields the best results.

Assigned Positive and Negative Controls

The following positive and negative controls should be included in a PCR run:
Master Mix control (DNA negative control). This is a PCR in which no DNA is added to the reaction. When the expected result, no PCR products, is observed this indicates that the PCR cocktail was not contaminated with target DNA.
A DNA positive control (genomic DNA sample known to contain the transgenic sequences). Successful amplification of this positive control demonstrates that the PCR was run under conditions which allow for the amplification of target sequences.
A wildtype DNA control. This is a PCR in which the template DNA provided is genomic DNA prepared from a non-transgenic plant. When the expected result, no amplification of the transgene PCR product but amplification of the endogenous PCR product, is observed this indicates that there is no detectable transgene background amplification in a genomic DNA sample.

Primers

The following primers, which specifically recognize the transgene and a flanking sequence of GAT-OS2 are used:

| | | |
|---|---|---|
| OSAO3: | 5'-gAC.TCT.gTA.TgA.ACT.gTT.CgC-3'<br>(target: P35S) | (SEQ ID 4) |
| OSAO4: | 5'-TCg.CAT.ATg.TAT.gTA.ACA.CgC-3'<br>(target: plant DNA) | (SEQ ID 5) |

Primers targeting an endogenous sequence are always included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers used are:

| | | |
|---|---|---|
| OSAO1: | 5'-gAT.CAg.TgC.Agg.CAA.TAC.Tgg-3'<br>(Phospholipase D gene Acc. No. AB001919,<br>3836 → 3856) | (SEQ ID 6) |
| OSAO2: | 5'-TTC.CTA.ACA.TgT.ggg.TgT.Cg-3'<br>(Phospholipase D gene Acc. No. AB001919,<br>4291 → 4272) | (SEQ ID 7) |

Amplified Fragments

The expected amplified fragments in the PCR reaction are:

For primer pair OSA01-OSA002: 457bp (endogenous control)

For primer pair OSA03-OSA004: 313bp (GAT-OS2 Elite Event)

PCR Conditions

The PCR mix for 50 µl reactions contains:

5 µl template DNA

5 µl 10×Amplification Buffer (supplied with Taq polymerase)

1 µl 10 mM dNTP's

1 µl OSA01 (10pmoles/µl)

1 µl OSA02 (10pmoles/µl)

2 µl OSA03 (10pmoles/µl)

2 µl OSA04 (10pmoles/µl)

0.2 µl Taq DNA polymerase (5 units/µl)

water up to 50 µl

The thermocycling profile to be followed for optimal results is the following:

| | |
|---|---|
| | 4 min. at 95° C. |
| Followed by: | 1 min. at 95° C. |
| | 1 min. at 57° C. |
| | 2 min. at 72° C. |
| | For 5 cycles |
| Followed by: | 30 sec. at 92° C. |
| | 30 sec. at 57° C. |
| | 1 min. at 72° C. |
| | For 22 to 25 cycles |
| Followed by: | 5 minutes at 72° C. |

Agarose Gel Analysis

Between 10 and 20 µl of the PCR samples should be applied on a 1.5% agarose gel (Tris-borate buffer) with an appropriate molecular weight marker (e.g. 100 bp ladder PHARMACIA).

Validation of the Results

Data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

Lanes showing visible amounts of the transgenic and endogenous PCR products of the expected sizes, indicate that the corresponding plant from which the genomic template DNA was prepared, has inherited the GAT-OS2 elite event. Lanes not showing visible amounts of the transgenic PCR product and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn'allow for a PCR product to be generated. These plants cannot be scored. The genomic DNA preparation should be repeated and a new PCR run, with the appropriate controls, has to be performed.

Use of Discriminating PCR Protocol to Identify GAT-OS2

Rice leaf material from plants comprising different transgenic events (samples 1 to 10) was tested according to the above-described protocol. Samples from M202 wild-type and Bengal wild-type were taken as negative controls.

Figure 2:
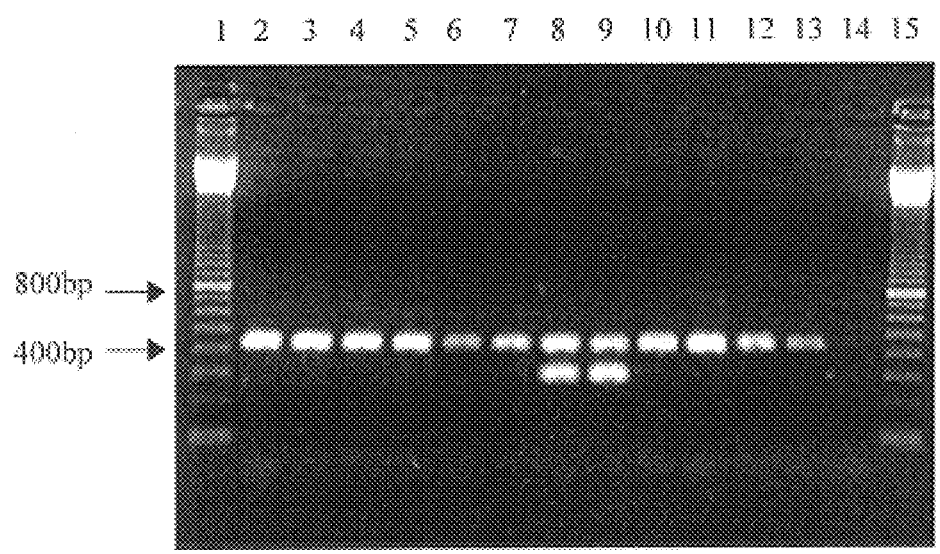
FIG. 2. PCR analysis of different lines using the GAT-OS2 PCR identification protocol. Loading sequence of the gel: lane 1, molecular weight marker (100 bp ladder), lanes 2 to 11, DNA samples from rice plants comprising different transgenic events, lane 12, DNA from M202 wild-type, lane 13, DNA from Bengal wild-type, lane 14, negative control (water), lane 15, molecular weight marker (100 bp ladder).

The results of the PCR analysis are illustrated in FIG. 2. Samples 8 and 9 (which in fact contained DNA from plants derived from the same event) are recognized as comprising elite event GAT-OS2. All other tested lines do not comprise this elite event.

Example 4

Introgression of GAT-OS2 into Preferred Cultivars

Elite event GAT-OS2 is introduced by repeated back-crossing into the following cultivars:

California Temperate Japonicas (such as but not limited to M204, M202, M201, M103)

California Tropical Japonicas (such as but not limited to L201, L202)

Japanese and Korean Temperate Japonicas (such as but not limited to Koshihikari and Milyang)

Australian Temperate Japonicas (such as but not limited to Millin and Jarrah)

Mediterranean Temperate Japonicas (such as but not limited to Ballila, Arborio)

Chinese Indicas (such as but not limited to Guichao, Congui 314, Teqing)

Southern United State Tropical Japonicas, long grain (such as but not limited to Drew, Cypress, Jefferson, Priscilla, Cocadrie)

Southern United State Tropical Japonicas, medium grain (such as but not limited to Bengal, Mars, Brazos, Mercury)

South American Tropical Japonicas, long grain (such as but not limited to El Paso 144, IRGA 409)

Far Eastern basmati and jasmine types (Kasmir, Kwao Dak Mali)

African javanica types (bulu rices)

It is observed that the introgression of the elite event into these cultivars does not significantly influence any of the desirable phenotypic or agronomic characteristics of these cultivars (no linkage drag) while expression of the transgene, as determined by glufosinate tolerance, meets commercially acceptable levels. This confirms the status of event GAT-OS2 as an elite event.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Seed comprising elite event GAT-OS2 was deposited as GAT-OS2 at the ATCC (American Type Culture Collection, 10801 University Blvd, Manassas, Va. 20110-2209) under number: ATCC 203352, under the terms of the Budapest Treaty (2500 seeds), on Oct. 19, 1998.

What is claimed is:

1. A transgenic, glufosinate tolerant rice plant, cell, tissue or seed, which is characterized in that the genomic DNA of said plant, cell, tissue or seed yeilds a DNA fragment of between 290 and 350 bp, in the GAT-OS2 Elite event Polymerase Chain Reaction identification protocol.

2. The plant, cell, tissue or seed of claim 1, which is characterized in that a DNA fragment of about 313 bp, is amplified from the genomic DNA of said plant, cell, tissue or seed in the GAT-OS2 Elite event Polymerase Chain Reaction identification protocol.

3. The plant, cell, tissue or seed of claim 1, which is characterized in that genomic DNA of said plant, cell, tissue or seed yields, when analyzed according to the GAT-OS2 Elite event Restriction map identification protocol, at least three restriction fragments or pairs of restriction fragments, wherein said restriction fragments or pairs of restriction fragments are selected from the group of:

i. one EcoRI fragment with a length between 1159 and 1700 bp;

ii. one pair of BamHI fragments wherein one has a length between 805 and 1093 bp and the other has a length between 1700 and 2140 bp;

iii. one pair of EcoRV fragments wherein one has a length between 2838 and 4507 bp and the other has a length of more than 5077 bp;

iv. one Hind III fragment with a length between 5077 and 11497 bp;

v. one pair of NcoI fragments both with lengths between 2838 and 4507 bp; and vi one NsiI fragment with a length between 4749 and 11497 bp;

wherein each of said restriction fragments hybridize, under standard stringency conditions, with the 1327 bp fragment obtained by EcoRI digestion of the plasmid having the nucleotide sequence of SEQ ID NO:8.

4. The plant, cell, tissue or seed of claim 3, which is characterized in that genomic DNA of said plant, cell, tissue or seed yields, in the GAT-OS2 Elite event Restriction map identification protocol, at least four restriction fragments or pairs of restriction fiagments selected from said group.

5. The plant, cell, tissue or seed of claim 4, which is characterized in that genomic DNA of said plant, cell, tissue or seed yields, in the GAT-OS2 Elite event Restriction map identification protocol, at least five restriction fragments or pairs of restriction fragments selected from said group.

6. The plant, cell, tissue or seed of claim 5, which is characterized in that genomic DNA of said plant, cell, tissue or seed yields, in the GAT-OS2 Elite event Restriction map identification protocol, the six restriction fragments or pairs of restriction fragments selected from said group.

7. A plant which is grown from a seed deposited at the ATCC under number ATCC 203352.

8. A cell or tissue of the plant of claim 7.

9. A seed deposited at the ATCC under number 203352.

10. A transgenic, glufosinate tolerant rice plant which is obtained by propagation of, and/or breeding with, a rice plant grown from a seed deposited at the ATCC under the number 203352, which is characterized in that the genomic DNA of said plant, or gemomic DNA of a cell, tissue or seed of said plant yields a DNA fragment of between 290 and 350 bp, in the GAT-OS2 Elite event Polymerase Chain Reaction identification protocol.

11. A process for cultivating rice plants which comprises growing plants of any one of claims 1 to 6 or 8.

12. The process of claim 11 which further comprises applying a herbicide with glufosinate as an active ingredient to the cultivated rice plants.

13. A process for breeding rice which comprises crossing a plant of any one of claims 1 to 6 or 7 with another rice plant.

14. A process for producing the transgenic glufosinate tolerant rice cell according to claim 1 which comprises inserting a recombinant DNA molecule into a part of the chromosomal DNA of a rice cell comprising the sequence of SEQ ID NO:9.

15. A transgenic rice seed comprising elite event GAT-OS2, seed comprising GAT-OS2 being deposited as ATCC accession number 203352.

16. A process for producing the transgenic glufosinate tolerant rice plant according to claim 1 which comprises inserting a recombinant DNA molecule into a part of the chromosomal DNA of a rice cell characterized by the sequence of SEQ ID NO:9 and regenerating a rice plant from the transformed rice cell.

17. A transgenic rice plant obtainable by the method of claim 16.

18. A glufosinate tolerant rice plant obtained by propagation of and/or breeding with a rice plant grown from seed deposited at the ATCC under number 203352; said glufosinate tolerant rice plant having all the identifying characteristics of the rice plant grown from the seed deposited at the ATCC under number 203352.

19. A rice plant grown from the seed of claim 15 or a cell or tissue from said rice plant.

* * * * *

UNITED STATES PATENT AND TRADEMARK OFFICE
CERTIFICATE OF CORRECTION

PATENT NO.    : 6,333,449 B1
DATED         : December 25, 2001
INVENTOR(S)   : Michiels et al.

It is certified that error appears in the above-identified patent and that said Letters Patent is hereby corrected as shown below:

<u>Column 28,</u>
Line 29, please change "any one of claims 1 to 6 or 8" to -- any one of claims 1 to 6 or 7 --.

Signed and Sealed this

Eighteenth Day of March, 2003

JAMES E. ROGAN
*Director of the United States Patent and Trademark Office*